US006833365B2

(12) United States Patent
Levy et al.

(10) Patent No.: US 6,833,365 B2
(45) Date of Patent: Dec. 21, 2004

(54) **TETRACYCLINE COMPOUNDS FOR TREATMENT OF *CRYPTOSPORIDIUM PARVUM* RELATED DISORDERS**

(75) Inventors: Stuart B. Levy, Boston, MA (US); Mark L. Nelson, Wellesley, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/768,189

(22) Filed: Jan. 23, 2001

(65) Prior Publication Data

US 2002/0115644 A1 Aug. 22, 2002

Related U.S. Application Data

(60) Provisional application No. 60/178,519, filed on Jan. 24, 2000.

(51) Int. Cl.[7] .................... A61K 31/65
(52) U.S. Cl. .................... 514/152
(58) Field of Search .................... 514/152, 567; 552/203, 205

(56) References Cited

U.S. PATENT DOCUMENTS

| | | | | |
|---|---|---|---|---|
| 2,980,584 | A | 4/1961 | Hammer | 167/65 |
| 2,990,331 | A | 6/1961 | Neumann et al. | 167/65 |
| 3,062,717 | A | 11/1962 | Hammer | 167/65 |
| 3,165,531 | A | 1/1965 | Blackwood et al. | 260/330.5 |
| 3,454,697 | A | 7/1969 | Joyner et al. | 424/227 |
| 3,557,280 | A | 1/1971 | Weber et al. | 424/80 |
| 3,674,859 | A | 7/1972 | Beutel et al. | 424/80 |
| 3,957,980 | A | 5/1976 | Noseworthy | 424/227 |
| 4,018,889 | A | 4/1977 | Armstrong | 424/80 |
| 4,024,272 | A | 5/1977 | Rogalski et al. | 424/275 |
| 4,126,680 | A | 11/1978 | Armstrong | 424/80 |
| 5,532,227 | A | 7/1996 | Golub et al. | 514/152 |
| 5,639,742 | A | 6/1997 | Lee et al. | 514/152 |
| 5,789,395 | A | 8/1998 | Amin et al. | 514/152 |
| 5,834,450 | A | 11/1998 | Su | 514/152 |

FOREIGN PATENT DOCUMENTS

| | | |
|---|---|---|
| WO | WO 9308806 | 5/1993 |
| WO | WO 9937306 | 7/1999 |

OTHER PUBLICATIONS

Armson et al., "Assessment of drugs against *Cryptospordium parvum* using a simple in vitro screening method." FEMS Microbiology Letters, vol. 178, pp. 227–233, 1999.*

Armson A., et al. "Assessment of drugs against *Cryptosporidium parvum* using a simple in vitro screening metho," *FEMS Microbiol Lett.* Sep. 15, 1999;178(2):227–33.

Brites C., et al. "Multiple drug regimen for severe diarrhea associated with *Cryptosporidium* in AIDS patients," *Rev Soc Bras Med Trop.* Apr.–Jun. 1991;24(2):117.

Current, W.L. et al., "A comparison of endogenous development of three isolates of *cryptosporidium* in suckling mice," *J. Protozoology* 33:98–108 (1986).

Current, W.L. et al., "Cryptosporidiosis," *Clin Microbiol. Rev.* 4(3):325–358 (1991).

Fayer, R., et al., "Glycoside antibiotics alone and combined with tetracyclines for prophylaxis of experimental cryptoporidiosis in neonatal BALB/c mice," *J Parasitol.* Aug. 1993;79(4):553–8.

Fitchenbaum, C.J. et al., "Use of paromomycin for treatment of cryptosporidiosis in patients with aids," *Clinical Infectious Diseases* 16:298 (1993).

Flanigan T.P., et al. "Cryptosporidia," *Prog. Clin Parasitol.* 3:1 (1993).

Keusch, G.T. et al., "Cryptosporidia—Who is at risk?," *Schweiz Med Wochenschr.* 125(18):899–908 (1995).

Nelson, M.L. et al., "Inhibition of the tetracycline efflux antiport protein by 13–thio–substituted 5–hydroxy– 6–deoxytetracyclines," *J. Med. Chem.* 36(3):370–377 (1993).

Peterson, C., "Cryptosporidiosis in patients infected with the human immunodeficiencyvirus," *Clin. Infec. Dis.* 15:903 (1992).

Tzipori, S. et al. "Chronic cryptosporidial diarrhoea and hyperimmune cow colostrum," *Lancet* 2(8554):344 (1987).

Tzipori, S., "Cryptosporidiosis in perspective," *Advances in Parasitology* 27:63–129 (1988).

Ungar, B.L.P. et al., "Cessation of *cryptosporidium*–associated diarrhea in an acquired immunodeficiency syndrome patient after treatment with hyperimmune bovine colostrum," *Gastroenterology* 98:486–489 (1990).

* cited by examiner

*Primary Examiner*—Barbara P. Badio
(74) *Attorney, Agent, or Firm*—Lahive & Cockfield, LLP; Elizabeth A. Hanley, Esq.; Cynthia M. Soroos, Esq.

(57) ABSTRACT

Methods and compositions for treating *Cryptosporidium parvum* related disorders in a mammal are discussed. Several novel tetracycline compounds useful for treating *Cryptosporidium parvum* related disorders are also included.

38 Claims, No Drawings

TETRACYCLINE COMPOUNDS FOR TREATMENT OF *CRYPTOSPORIDIUM PARVUM* RELATED DISORDERS

RELATED APPLICATIONS

This application claims priority to U.S. Provisional Patent Application Ser. No. 60/178,519, entitled "Tetracycline Compounds for Treatment of *Cryptosporidium Parvum* Related Disorders," filed on Jan. 24, 2000, the entire contents of which are hereby incorporated herein by reference. The present application is related to U.S. patent application Ser. No. 09/234,847, entitled "Pharmaceutically Active Compounds and Methods of Use Thereof" filed on Jan. 22, 1999, and U.S. Provisional Patent Application Ser. No. 60/154,701, entitled "Methods Of Preparing Substituted Tetracyclines With Transition Metal-Based Chemistries" filed on Sep. 14, 1999. The entire contents of both applications are hereby expressly incorporated herein by reference.

BACKGROUND OF THE INVENTION

*Cryptosporidium parvum* (or *C. parvum*) is an enteric protozoa of the phylum Apicomplexa. It is a major cause of diarrhea in humans and certain domestic animals (Tzipori, *Advances in Parasitology* (1988) 27:63–129). It is responsible for sporadic cases and major waterborne outbreaks of self-limiting diarrhea in immunocompetent humans (Current, W. L. et al., *Clinical Microbiology Reviews*, (1991) 4:325). *C. parvum* is one of several important opportunistic infections (OI) associated with diarrhea and wasting in patients with AIDS. Depending on location in the United States, some 10 to 15% of individuals with AIDS contract the disease (Peterson, *Clinical Infectious Diseases*, (1992) 15:903). The infection in the immunodeficient host often becomes persistent, causing life-threatening, profound, unremitting watery diarrhea and wasting. A prolonged course of infection often leads to a spread of infection into the hepatobiliary (HB) tract causing serious complications (Flanigan, *Progress in Clinical Parasitiology* (1993) 3:1). Of the OI affecting patients with AIDS, *C. parvum* is one of only a few infections against which there is no consistently effective treatment. There had been only a few reports of successful treatment of individual AIDS patients with hyperimmune bovine colostrum (Tzipori, *Lancet*. (1986) ii:344; Ungar, *Gastroenterology* (1990) 98:486) and with paromomycin (PRM) (Fitchenbaum, *Clinical Infectious Diseases* (1993) 16:298). Since none of the available antimicrobial agents are consistently effective, a search for novel therapeutic agents against *C. parvum* is necessary. With increased survival time of patients with AIDS due to much improved patient care, the incidence of the disease in this population is likely to continue to rise.

The lifecycle of *C. parvum* is similar to that of other coccidia which infect mammals. The lifecycle can be divided into six major developmental events (Current, *Journal of Protozoology*, (1986) 33:98); excystation, the release of infective sporozoites; merogony, the asexual multiplication within host cells; gametogony, the formation of micro and macrogametes; fertilization, the union of micro and macrogametes; oocyst wall formation, to produce an environmentally resistant stage that transmits infection from one host to another; and sporogony, the formation of infective sporozoites within the oocyst wall. Each intracellular stage of *C. parvum* resides within a parasitophorous vacuole confined to the microvillous region of the host cell, whereas comparable stages of *Toxoplasma gondii, Eimeria*, or *Isopora* to which *C. parvum* is closely related, occupy parasitophorous vacuoles deep within the host cytoplasm. Oocysts of *C. parvum* undergo sporogony while they are within the host cells and are infective when released in the feces. Approximately 20% of the oocysts of *C. parvum* are thin walled and discharge their sporozoites within the lumen of the same host, while 80% form a thick two-layered environmentally resistant oocyst wall, and are discharged in the feces. The four sporozoites emerging from the thin-walled oocysts and repeated cycles of schizogeny contribute to the persistence of the infection in the immunodeficient host known as autoinfection.

SUMMARY OF THE INVENTION

In one embodiment, the invention pertains to a method for controlling *Cryptosporidium parvum* in a mammal, by administering to the mammal an effective amount of a tetracycline compound. Examples of tetracycline compounds of the invention include compounds of formula I:

(I)

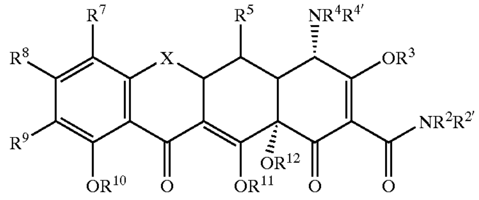

wherein:

X is $CHC(R^{13}Y'Y)$, $CHR^6$, S, $NR^6$, or O;

$R^2$, $R^4$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxy, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, or an arylalkyl;

$R^6$, $R^7$, $R^8$ and $R^9$ are each independently hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

and pharmaceutically acceptable salts thereof.

The invention also pertains to a method for treating a *Cryptosporidium parvum* related disorder in a mammal, by administering to the mammal an effective amount of a tetracycline compound. In an embodiment, the tetracycline compound is of formula (I). In another advantageous embodiment, the mammal is immunocompromised, e.g., suffering from AIDS or undergoing chemotherapy. Preferably, the mammal is a human.

In another embodiment, the invention pertains to pharmaceutical compositions containing an effective amount of a tetracycline compound to treat a *Cryptosporidium parvum* related disorder in a mammal and a pharmaceutically acceptable carrier.

In yet another embodiment, the invention features a tetracycline compound of the formula:

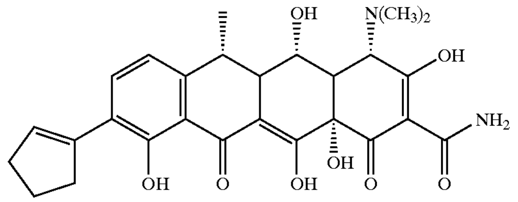

DETAILED DESCRIPTION OF THE INVENTION

The invention pertains, at least in part to methods for controlling *Cryptosporidium parvum* in a mammal, by administering to the mammal an effective amount of a tetracycline compound.

*Cryptosporidium* is a coccidian protozoan parasite that has gained much attention in the last 20 years as a clinically important human pathogen. For several decades, *Cryptosporidium* was thought to be a rare, opportunistic animal pathogen, but the first case of human cryptosporidiosis in 1976 involved a 3-year-old girl from rural Tennessee who suffered severe gastroenteritis for two weeks (Flanigan *Prog Clin Parasitol* (1993) 1). Electron microscopic examination of the intestinal mucosa led to the discovery that *Cryptosporidium parvum* was the infectious species in humans. In the early 1980s, the strong association between cases of cryptosporidiosis and immunodeficient individuals (such as those with AIDS—acquired immunodeficiency syndrome) brought *Cryptosporidium* to the forefront as a ubiquitous human pathogen. Presently, the increasing population of immunocompromised patients and the various outbreaks of cryptosporidiosis through infection by water-borne *Cryptosporidium* oocysts (often in drinking water) have created world wide interest in this pathogen. Unlike other intestinal pathogens, *Cryptosporidium* can infect several different hosts, can survive most environments for long periods of time (Keusch, et al. *Schweiz Med Wochenschr*, (1995) 125(18):899), and inhabit all climates and locales.

The terms "tetracycline" or "tetracycline derivative" compounds include tetracycline and other tetracycline family members such as, chlortetracycline, oxytetracycline, demeclocycline, methacycline, doxycycline, minocycline, and sancycline. Additional tetracycline compounds can be found, for example, in U.S. patent application Ser. No. 09/234,847, and U.S. Pat. Nos. 5,834,450; 5,532,227; 5,789,395; 5,639,742 and German patents DE 28 14 974 and DE 28 20 983. The entire contents of the aforementioned applications and patents are hereby expressly incorporated herein by reference.

More recent research efforts have focused on developing new tetracycline antibiotic compositions effective under varying therapeutic conditions and routes of administration; and for developing new tetracycline analogues which might prove to be equal or more effective than the originally introduced tetracycline families beginning in 1948. Representative of such developments include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These issued patents are merely representative of the range of diversity of investigations seeking tetracycline and tetracycline analogue compositions which are pharmacologically active, and the contents of each are expressly incorporated by reference.

Historically, soon after their initial development and introduction, the tetracyclines, regardless of specific formulation or chemical structure, were found to be highly effective pharmacologically against rickettsiae, a number of gram-positive and gram-negative bacteria, and the agents responsible for lymphogranuloma venereum, including conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as antibiotics of choice.

In one embodiment, the tetracycline compound of the invention inhibits more than 70% of *Cryptosporidium parvum* at a concentration less than 100 $\mu$g/ml, less than 50 $\mu$g/ml, less than 20 $\mu$g/ml, less than 10 $\mu$g/ml, or less than 1 $\mu$g/ml. The inhibition of *Cryptosporidium parvum* can be tested using the assay described in Example 2.

Tetracycline compounds of the invention include compounds of Formula I:

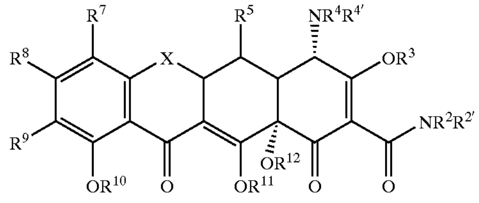

(I)

wherein:

X is $CHC(R^{13}Y'Y)$, $CHR^6$, S, $NR^6$ or O;

$R^2$, $R^4$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydroxy, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, or an arylalkyl;

$R^6$, $R^7$, $R^8$ and $R^9$ are each independently hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl, alkenyl, alkynyl, alkoxy, alkylthio, alkylsulfinyl, alkylsulfonyl, alkylamino, or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or arylalkyl; and pharmaceutically acceptable salts thereof.

In one further embodiment, $R^{2'}$, $R^3$, $R^{10}$, $R^{11}$, and $R^{12}$ are each hydrogen or a prodrug moiety. Furthermore, $R^4$ and $R^{4'}$ can be alkyl, e.g., lower alkyl, e.g., methyl, ethyl, propyl, or butyl. In another embodiment, $R^5$ is hydroxyl, hydrogen, or alkanoyl, e.g., an ester, advantageously, a propanoic ester. In yet another embodiment, X is S or $CHR^6$. Examples of $R^6$ include alkyl groups, e.g., methyl, ethyl, propyl, or halogens or hydroxyl groups. Advantageously, $R^6$ may comprise a heteroatom, such as, for example, a sulfur atom. For example, $R^6$ may be a thioether, e.g., a cyclopentylthio ether. Advantageously examples of $R^9$ include hydrogen atoms, and alkyl (e.g., t-butyl) and alkenyl (e.g., cyclopentenyl) groups.

Tetracycline compounds of the invention include, for example, compounds of the formulae:

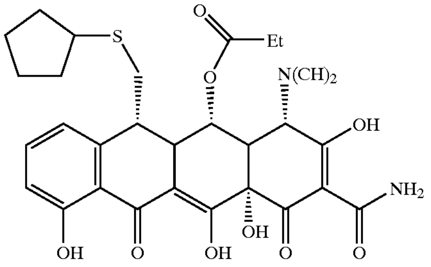

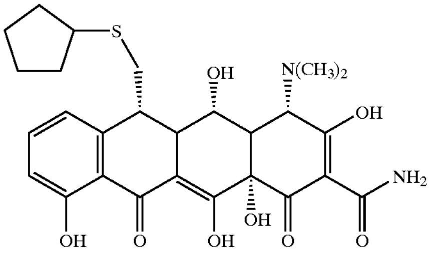

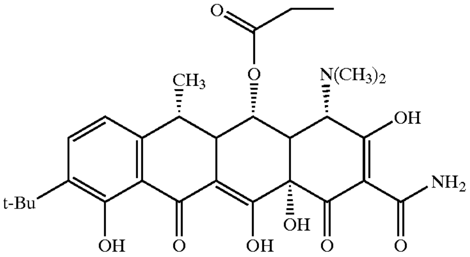

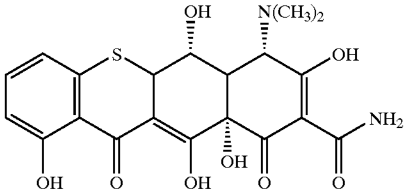

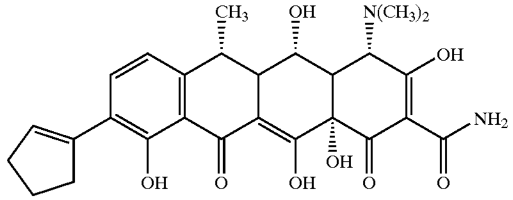

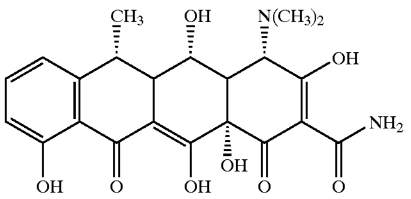

-continued

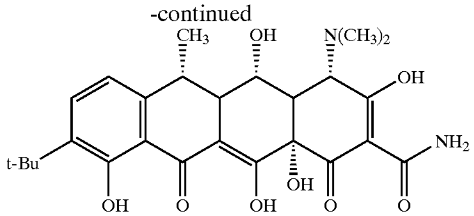

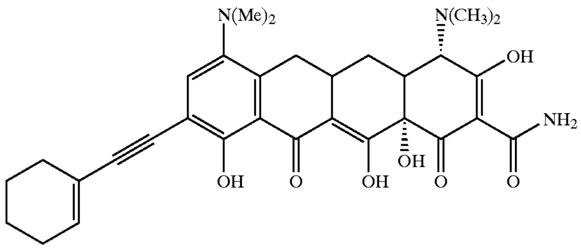

Other examples of preferred tetracycline compounds of the invention include, for example, 5-propionyl-6-cyclopentylsulfanylmethyl doxycycline; thiatetracycline; 9-cyclopent-1-enyl-doxycycline; 5-propionyl-9-tert-butyl-doxycycline; doxycycline; 9-tert-butyl doxycycline; 9-cyclohex-1-enylethynyl minocycline; and 6-cyclopentylsulfanylmethyl doxycycline.

The tetracycline compounds of the invention can be synthesized using the methods described in Example 1. Scheme 1 depicts a general synthesis of a thiol ether from methacycline.

SCHEME1

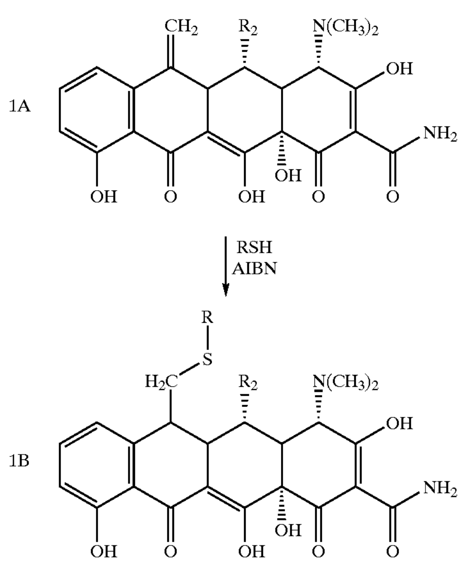

13-substituted thiols can be synthesized by the method outlined in Scheme 1, above. The synthesis of the compounds is described in greater detail in Example 1. Generally, 13-substituted thiol ethers (1B) can be synthesized by heating a tetracycline salt (such as methacycline hydrochloride, 1A), AIBN (2,2'-azobisisobutyronitrile), and a thiol in ethanol at reflux for six hours under an inert atmosphere.

9-substituted tetracyclines such as 9-cyclopentenyl doxycycline can be synthesized by the method shown in Scheme 2. As in Scheme 2, 9-substituted tetracycline compounds can be synthesized by treating a tetracycline compound (e.g., doxycycline, 2A), with sulfuric acid and sodium nitrate. The resulting product is a mixture of the 7-nitro and 9-nitro isomers (2B and 2C, respectively). The 7-nitro (2B) and 9-nitro (2C) derivatives are treated by hydrogenation using hydrogen gas and a platinum catalyst to yield amines 2D and 2E. The isomers are separated at this time by conventional methods. To synthesize 9-substituted alkenyl derivatives, the 9-amino tetracycline compound (2E) is treated with HONO, to yield the diazonium salt (2F). The salt (2F) is treated with an appropriate halogenated reagent (e.g., $R^9Br$, wherein $R^9$ is an aryl, alkenyl, or alkynyl moiety) to yield the desired compound (e.g., in Scheme 2, 9-cyclopent-1-enyl doxycycline (2G)).

carbons of the hydrocarbon backbone, e.g., oxygen, nitrogen, sulfur or phosphorous atoms. In preferred embodiments, a straight chain or branched chain alkenyl group has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkenyl groups have from 4–7 carbon atoms in their ring structure, and more preferably have 5 or 6 carbons in the ring structure, e.g., cyclopentene or cyclohexene.

The term "alkyl" includes saturated aliphatic groups, including straight-chain alkyl groups, branched-chain alkyl groups, cycloalkyl (alicyclic) groups, alkyl substituted

SCHEME 2

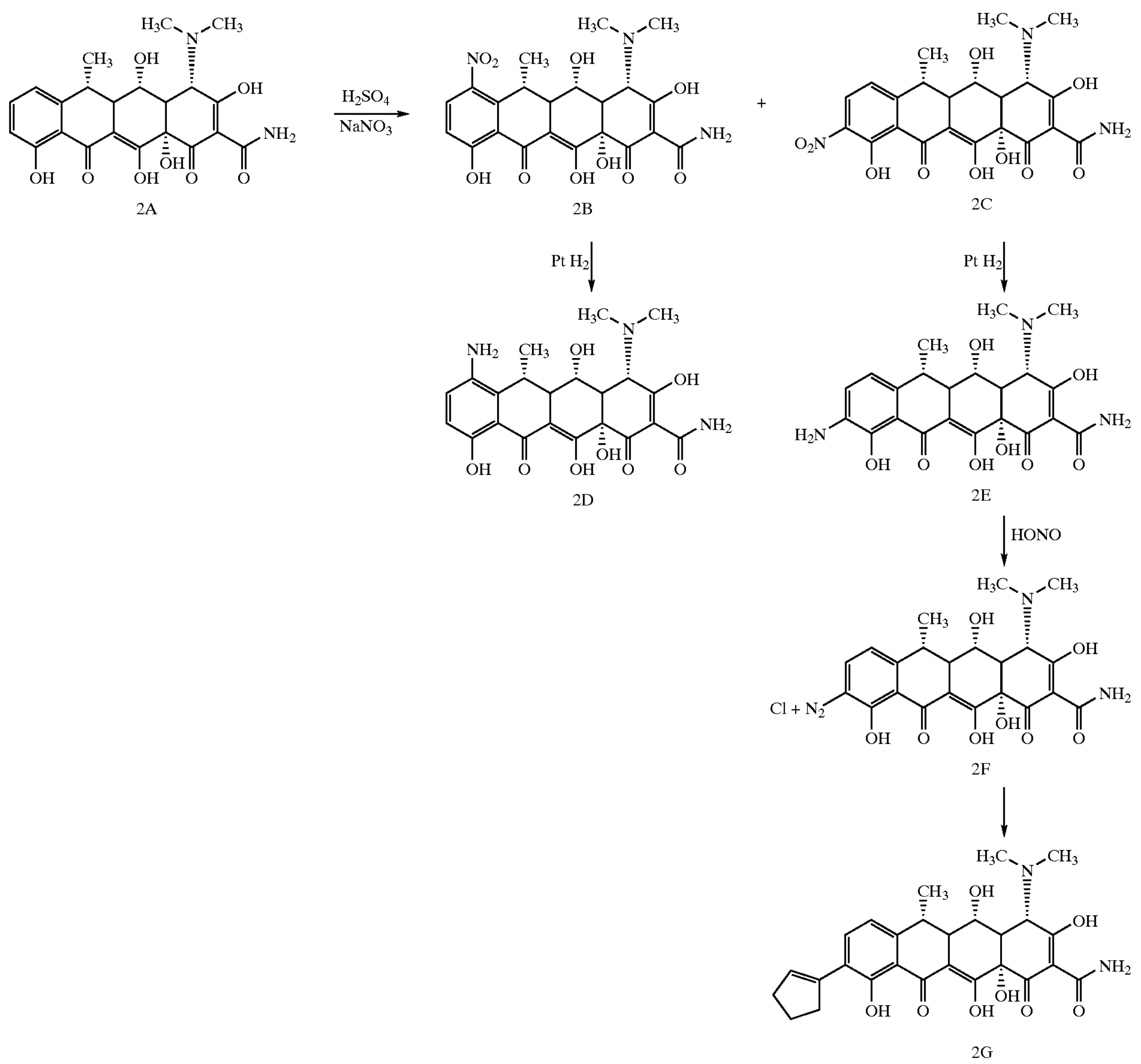

The term "alkenyl" includes unsaturated aliphatic groups, including straight-chain alkenyl groups, branched-chain alkenyl groups, cycloalkenyl (alicyclic) groups, alkenyl substituted cycloalkyl or cycloalkenyl groups, and cycloalkenyl substituted alkyl or alkenyl groups. The term alkenyl further includes alkenyl groups, which can further include oxygen, nitrogen, sulfur or phosphorous atoms replacing one or more cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkyls have from 4–7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively. Examples of substituents of alkynyl groups include, for example alkyl, alkenyl (e.g., cycloalkenyl, e.g., cyclohenxenyl), and aryl groups.

Unless the number of carbons is otherwise specified, "lower alkyl" as used herein means an alkyl group, as defined above, but having from one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "alkylsulfinyl" include groups which have one or more sulfinyl (SO) linkages, typically 1 to about 5 or 6 sulfinyl linkages. Advantageous alkylsulfinyl groups include groups having 1 to about 12 carbon atoms, preferably from 1 to about 6 carbon atoms.

The term "alkylsulfonyl" includes groups which have one or more sulfonyl ($SO_2$) linkages, typically 1 to about 5 or 6 sulfonyl linkages. Advantageous alkylsulfonyl groups include groups having 1 to about 12 carbon atoms, preferably from 1 to about 6 carbon atoms.

The term "alkanoyl" includes groups having 1 to about 4 or 5 carbonyl groups. The term "aroyl" includes aryl groups, such as phenyl and other carbocyclic aryls, which have carbonyl substituents. The term "alkaroyl" includes aryl groups with alkylcarbonyl substituents, e.g., phenylacetyl.

The structures of some of the tetracycline compounds of this invention include asymmetric carbon atoms. The isomers arising from the chiral atoms (e.g., all enantiomers and diastereomers) are included within the scope of this invention, unless indicated otherwise. Such isomers can be obtained in substantially pure form by classical separation techniques and by stereochemically controlled synthesis.

The invention also pertains to a pharmaceutical composition containing an effective amount of a tetracycline compound to treat or prevent a *Cryptosporidium parvum* related disorder in a mammal and a pharmaceutically acceptable carrier. The pharmaceutical composition may contain an effective amount of a supplementary anti-*Cryptosporidium parvum* agent.

The language "pharmaceutically acceptable carrier" includes substances capable of being coadministered with the tetracycline compound(s), and which allows the tetracycline compounds to perform their intended function, e.g., treating a *Cryptosporidium parvum* related disorder or preventing a *Cryptosporidium parvum* related disorder. Examples of such carriers include solutions, solvents, dispersion media, delay agents, emulsions and the like. The use of such media for pharmaceutically active substances are well known in the art. Any other conventional carrier suitable for use with the tetracycline compounds of the present invention are included.

For example, one or more compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

At least many of the tetracycline compounds of the invention suitably may be administered to a subject in a protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an appropriate acidic group is present on a compound of the invention, a pharmaceutically acceptable salt of an organic or inorganic base can be employed such as an ammonium salt, or salt of an organic amine, or a salt of an alkali metal or alkaline earth metal such as a potassium, calcium or sodium salt.

Therapeutic compounds can be administered to a subject in accordance with the invention by any of a variety of routes. Topical (including transdermal, buccal or sublingual), and parenteral (including intraperitoneal, subcutaneous, intravenous, intradermal or intramuscular injection) are generally preferred.

For parenteral application, particularly suitable are solutions, preferably oily or aqueous solutions as well as suspensions, emulsions, or implants, including suppositories. Therapeutic compounds will be formulated in sterile form in multiple or single dose formats such as being dispersed in a fluid carrier such as sterile physiological saline or 5% saline dextrose solutions commonly used with injectables.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For topical applications, the tetracycline compound(s) can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

The actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

The language "effective amount" of the tetracycline compound is that amount necessary or sufficient to control *Cryptosporidium parvum* in a mammal, e.g., prevent the various morphological and somatic symptoms of a *Cryptosporidium parvum*-related disorder. The effective amount can vary depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation. An in vivo assay as described in Example 4 below or an assay similar thereto (e.g., differing in choice of cell line or type of illness) also can be used to determine an "effective amount" of a tetracycline compound. The ordinarily skilled artisan would select an appropriate amount of a tetracycline compound for use in the aforementioned in vivo assay. Preferably, the effective amount of the tetracycline is effective to treat a mammal suffering from a *Cryptosporidium parvum* related disorder.

The term "mammal" includes animals which are capable of having a *Cryptosporidium parvum* related disorder. Examples of mammals include, but are not limited to, ruminants (e.g., cattle and goats), mice, rats, hamsters, dogs, cats, horses, pigs, sheep, lions, tigers, bears, monkeys, chimpanzees, and, in a preferred embodiment, humans. The mammal may be immunocompetent or immunocompromised, e.g., suffering from an immunodeficiency. For example, the mammal may have AIDS or may have previously or concurrently undergone chemotherapy.

In another embodiment, the mammal may be elderly or young. The mammal may or may not be suffering from a *Cryptosporidium parvum* related disorder. The tetracycline compounds may be administered to a mammal susceptible to a *Cryptosporidium parvum* disorder to prevent the occurrence of the disorder.

The language "*Cryptosporidium parvum* related disorder" includes disorders which are related to the infection or the presence of *Cryptosporidium parvum* in a mammal. Examples of *Cryptosporidium parvum* related disorders include diarrhea and cryptosporidiosis.

In another embodiment, the invention pertains to a method for treating a *Cryptosporidium parvum* related disorder in a mammal, by administering to the mammal an effective amount of a tetracycline compound such that said mammal is treated for the disorder.

In a further embodiment, the invention includes the administration of a supplementary anti-*Cryptosporidium parvum* agent in combination with the tetracycline compound of the invention.

The language "in combination with" includes simultaneous administration of the tetracycline compound of the invention and the supplementary anti-*Cryptosporidium parvum* agent, administration of the agent first, followed by the tetracycline compound and administration of the tetracycline compound first, followed by the agent. The invention also includes the administration of other therapeutic agents in combination with the tetracycline compounds of the invention. For example, the tetracycline compounds of the invention may be administered in combination with drugs used in AIDS therapy for AIDS patients.

The term "supplementary agent" includes compounds known in the art to have anti-*Cryptosporidium parvum* activity such as, for example, paromomycin and derivatives thereof.

The present invention is further illustrated by the following examples. These examples are provided to aid in the understanding of the invention and are not to be construed as limitations thereof.

EXEMPLIFICATION OF THE INVENTION

Example 1

Synthesis of Tetracycline Compounds

The following example discusses methods of synthesizing the tetracycline compounds of the invention.

Experimental

Melting points were taken on a Mel-Temp capillary melting point apparatus and are uncorrected. Nuclear magnetic resonance ($^1H$ NMR) spectra were recorded at 300 MHz on a Bruker Avance spectrometer. The chemical shift values are expressed in δ values (ppm) relative to tetramethylsilane or 3-(trimethylsilyl)-1-propanesulfonic acid, sodium salt, as either an internal or external standard using $CDCl_3$, DMSO-$d_6$, or MeOH-$d_4$ as the solvent. Column chromatography was performed according to the method of Still using Baker "flash" grade silica gel (40 $\mu$m) that was treated with a saturated solution of $Na_2$EDTA, washed with water, filtered and dried in an oven at 130° C. for three hours prior to use. Analytical TLC separations employed the use of 0.25 mm silica gel plates with florescence indicator obtained from J. T. Baker Chemical Co., Phillipsburg, N.J., that were pretreated by immersion into a saturated solution of $Na_2$EDTA for five minutes and reactivated at 130° C. for three hours. Solvent systems used were as follows: 50:50:5 $CHCl_3$/MeOH/5% $Na_2$EDTA (lower phase) (I), 65:20:5, $CHCl_3$/MeOH/$Na_2$EDTA (lower phase) (II). Visualization of TLC was accomplished by 0.5% aqueous Fast Blue BB salt and heating at 130° C. for 5 minutes. Analytical HPLC was performed on a Waters Bondapak C 18 reverse phase column by using two Varian SD 100 HPLC pumps at a 1.6 mL/min flow rate controlled by software. Detection was by UV absorption with Model 441 absorbance detector operating at 280 nm. Mobile phases used followed a linear gradient from 30% to 100% methanol over 30 minutes at 1.6 mL/min flow rate followed by isocratic elution with MeOH; solvent system A: 0.02 M $Na_2HPO_4$+0.001 M $Na_2$EDTA adjusted to pH 4.5 with $H_3PO_3$; solvent system B: 100% MeOH. Semipreparative HPLC separations used a Waters semipreparative C18 reverse-phase column at a flow rate of 6.4 mL/min. Low and high resolution mass spectra were performed on a PE Mariner spectrometer (Nelson et al., *J. Med. Chem.* (1993) 36(3):374).

General Procedure for the Synthesis of 13-[(Substituted phenyl)thio]-5-hydroxy-6-deoxytetracyclines 13-(Phenylthio)-5-hydroxy-6-α-deoxytetracycline A mixture of methacycline hydrochloride (3.0 g, 6.2 mmol), AIBN (250 mg), and thiophenol (1.32 g, 12.4 mmol) in ethanol (50 mL) was heated at reflux for 6 hours while under $N_2$. The reaction mixture was cooled, filtered to remove insolubles, and concentrated to one-fifth volume under reduced pressure. Precipitation of the resulting solution in cold $Et_2O$ led to isolation of crude product (2.17 g). The solid was dissolved in hot $H_2O$, and extracted into $CHCl_3$ at pH 5.0. Removal of the solid and treatment with activated charcoal in MeOH led to isolation of the product (0.958 g, 27.1%): mp=164–171° C.; TLC $R_f$=0.67 (I); HPLC $t_R$=14.45 min; $^1H$ NMR ($CDCl_3$) δ 11.9 (br s), 9.3 (br s), 7.35 (m, 6H), 6.83 (d, 1H), 6.74 (d, 1H) 5.95 (br s, 1H), 4.10 (br s, 1H), 3.82 (s, 2H), 3.60 (br s, 1H), 3.10 (m, 2H), 2.60 (m, 1H), 2.48 (s, 6H); MS (FAB) m/z 552,553 ([M+H]+); 445(M—$C_6H_5$—S+H).

13-(Cyclopentylthio)-5-hydroxy-6-α-deoxytetracycline

Methacycline hydrochloride (5.0 g, 10.4 mmol) was placed in a round-bottomed flask and suspended in 100 mL of ethanol. Twenty milliliters of cyclopentanethiol (0.0270 mol) and AIBN (250 mg) were added, and the reaction mixture was refluxed with stirring for 12 hours while under $N_2$. The mixture was reduced to one-fifth volume by distillation and filtered. The filtrate was dripped slowly into cold $Et_2O$ with stirring, resulting in the formation of a yellow precipitate. The compound was purified further by either column chromatography on EDTA-silica, by extraction at pH 4.5 into $CH_2Cl_2$, or by HPLC chromatography. An analytical sample was produced by HPLC as a yellow solid in moderate yield (28.3%). Higher yields were obtained by the extraction method and treatment with activated charcoal in MeOH (32.1%). mp=132–139° C.; TLC $R_f$=0.80 (I); HPLC $t_R$=21.19 min; $^1H$ NMR (MeOH-$d_4$) δ 7.38 (t, 1H), 7.02 (d, 1H), 6.72 (d, 1H), 4.10 (s, 2H), 2.70 (br s, 6H), 1.81–2.01 (br m, 2H), 1.28–1.75 (br m, 6H); HRMS (FAB)

calculated for $C_{27}H_{32}N_2O_8S$ 545.1957 (M+1), found 545.1960 (M+1).

[4S-(4α,12aα)]-9-(nitro)-4-(dimethylamino)-1,4,4a,5,5a,6,11,12a-octahydro-3,5,10,12,12a-pentahydroxy-6-methyl-1,11-dioxo-2-naphthacenecarboxamide To an ice cold solution of 1.0 g of doxycycline hydrochloride in 10 ml of concentrated sulfuric acid was added 0.231 g of potassium nitrate. The reaction was stirred for 1 hour under ambient atmosphere. The mixture was then poured over 150 g of ice and the resulting solid was extracted with n-butanol and dried to afford 0.9 g of the desired product as a yellow-green solid. MS(FAB): m/z 490 (M+H). $^1H$ NMR ($CD_3OD$): δ 7.50(d, 1H, J=8.07 Hz, H-8); 6.86(d, 1H, J=8.07 Hz, H-7); 4.44(bs, 1H, H-4); 3.62(dd, 1H, J=11.42; 8.35 Hz, H-5); 2.95 (bs, 6H), $NMe_2$); 2.81(d, 1H, J=11.45 Hz, H-4a); 2.71(dq, 1H, J=12.41; 6.5 Hz, H-6); 2.53(dd, 1H), J=12.23; 8.20 Hz, H-5a); 1.51(d, 3H, J=6.78 Hz, $CH_3$).

[4S-(4α,12aα)]-9-(amino)-4-(dimethylamino)-1,4,4a,5,5a,6,11,12a-octahydro-3,5,10,12,12a-pentahydrxy-6-methyl-1,11-dioxo-2-naphthacenecarboxamide Into a 200 ml hydrogenation bottle is added 1.0 g of compound 1, 40 ml of methanol, 1 ml of concentrated HCl, and 100 mg of 10% palladium on carbon. Using a hydrogenation apparatus, the mixture is subjected to 30 psi of hydrogen for 3 hours. The catalyst is filtered off and the filtrate is dried to afford 0.9 g of the dihydrochloride as a yellow solid. MS(FAB): m/z 460 (M+H). $^1H$ NMR ($CD_3OD$): d 7.54(d, 1H, J=8.08 Hz, H-8); 6.88(d, 1H, J=8.08 Hz, H-7); 5.16(dd, J=10.44; 7.94 Hz, H-5); 4.44(bs, 1H, H-4); 3.74(d, 1H, J=2.07 Hz, H-4); 3.04(bs, 6H, $NMe_2$); 2.90(dd, 1H, J=7.94; 2.07 Hz, H-4a); 2.72(dq, 1H, J=12.31; 6.56 Hz, H-6); 2.61(dd, 1H, J=12.31; 10.44 Hz, H-5a); 2.54(q, 2H, J=7.48 Hz, $CH_2$—C); 1.44(bs, 9H, $CMe_3$); 1.29(d, 3H, J=6.56 Hz, $CH_3$); 1.20(t, 3H, J=7.48 Hz, C-$CH_3$).

[4S-(4α,12aα)]-9-(diazonium)-4-(dimethylamino)-1,4,4a,5,5a,6,11,12a-octahydro-3,5,10,12,12a-pentahydroxy-6-methyl-1,11-dioxo-2-naphthacenecarboxamide A 10 ml roundbottom flask was charged with 100 mg of compound 2 and dissolved in 4 ml of 0.1 N methanolic hydrochloric acid. The solution was cooled to 0° C. and 35 μl of butyl nitrite was added with stirring. After 1 hour, the bright red reaction mixture was added dropwise to 100 ml of cold anhydrous diethyl ether. The product was collected by filtration, washed with ether, and dried in a vacuum dessicator to give 73 mg of the diazonium salt as an orange solid. MS(FAB): m/z 472 (M+H). $^1H$ NMR ($CD_3OD$): d 7.55(d, 1H, J=8.08 Hz, H-8); 6.86(d, 1H, J=8.08 Hz, H-7); 5.13(dd, J=10.44; 7.94 Hz, H-5); 4.41 (bs, 1H, H-4); 3.72(d, 1H, J=2.07 Hz, H-4); 3.04(bs, 6H, $NCH_3$); 2.90(dd, 1H, J=7.94; 2.07 Hz, H-4a); 2.70(dq, 1H, J=12.31; 6.56 Hz, H-6); 2.61(dd, 1H, J=12.31; 10.44 Hz, H-5a); 2.2(m, 6H, J=7.48 Hz, Acetyl); 1.44(bs, 9H, $C(CH_3)_3$); 1.29(d, 3H, J=6.56 Hz, $CH_3$); 1.20(t, 3H, J=7.48 Hz, C—$CH_3$).

General Procedure for Olefination

To a solution of 0.1 g of a 9-diazonium compound in wet methanol is added 0.05 equivalents of palladium acetate. The reaction mixture is stirred for 5 minutes at room temperature, and 2 equivalents of the desired olefin is added. Stirring is continued for 18 hours under ambient atmosphere or followed by HPLC. Upon completion, the catalyst is filtered off and the filtrate dried to give the crude product. The purified product is isolated by preparative reverse-phase HPLC using methanol and phosphate buffer gradient.

9-(1'-cyclopentenyl)minocycline

MS(FAB): m/z 511 (M+H).

Example 2

Assay for the Ability of Tetracycline Compounds to Control *Cryptosporidium parvum* Infection in Vitro This assay is designed to test the ability of a tetracycline compound to control *Cryptosporidium parvum* infection in vitro. The results show that tetracycline compounds of the invention can be used to control the growth of *C. parvum.*

MDCK cells were grown in 96-well microtiter plastic plates, and were seeded with approximately $5\times10^4$ cells per well, using DMEM as the growth/maintenance medium with 10% FCS. Plates were normally grown to confluence 2–3 days after having been seeded with bleached, less than four week-old, *C. parvum* oocysts. The *C. parvum* isolate used most often was the human-derived, calf-propagated GCH1 (Tzipori, *Clin. Diagn. Lab. Immunol.* (1994) 1:450; Tzipori, *J. Infect. Dis.* (1995) 172:1160). The DMEM medium was also added to the negative control wells. The tetracycline compounds and the oocysts were added to the wells concurrently. The cells were subsequently monitored twice daily and any apparent morphologic changes were recorded. The monolayers were fixed with methanol after 48 hour incubation at 37° C. in 8% $CO_2$.

Table 1 shows the Inhibition assay results of the tetracycline compounds in MDBK infected cells. The tetracycline compounds were used at various concentrations (0.1–2000 μg/mL) and were dissolved directly into the culture medium. A conventional indirect immunofluorecensce (IF) assay was used to detect and enumerate parasite forms after 48-hour incubation. For the purposes of this assay, a polyclonal rabbit anti-sporozoite antibody was produced. It was used at a dilution of 1:1000 and does not react with oocyst shells. The secondary antibody, a fluoroscein-conjugated goat anti-rabbit IgG, was used at a concentration of 1:100, according the manufacturer's instructions. The primary antibody was added after fixation for thirty minutes and after vigorous washing, the secondary antibody was incubated for another thirty minutes. The dried microtiter plate was viewed with an inverted microscope (×10 mag.), under ultraviolet light. For parasite counts, a semi-automated video imaging MCID system was used to facilitate the enumeration and analysis of the parasite data. In Table 1, good inhibition of *C. parvum* is indicated by '*' (e.g., 70% inhibition at concentrations above 10 μg/ml and above) and very good inhibition of *C. parvum* is indicated by '**' (e.g., 70% inhibition at concentrations below 10 μg/ml). Some compounds of the invention have 70% inhibition at concentrations below 1 μg/ml.

The study shows that all of the tetracycline compounds are capable of inhibiting or decreasing the amount *C. parvum* in a sample of cells.

TABLE 1
| Compound | Inhibition |
| --- | --- |
| 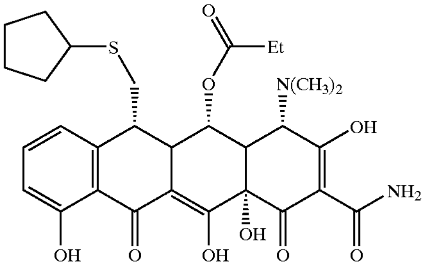 | ** |
| 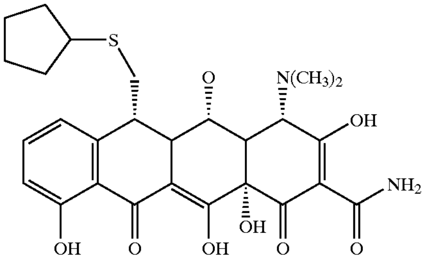 | ** |
| 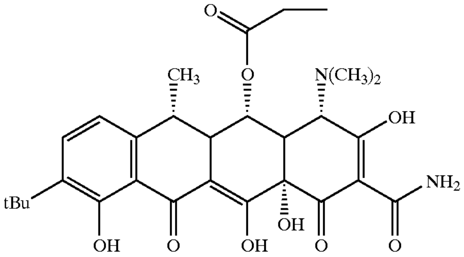 | * |
| 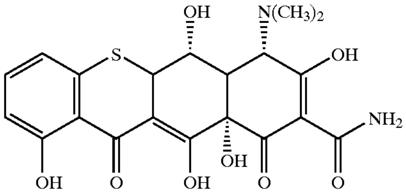 | * |
| 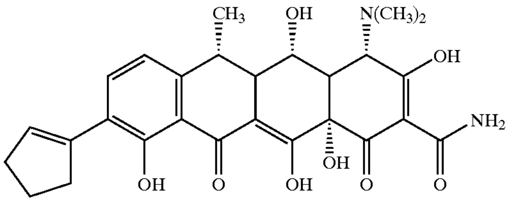 | ** |
| 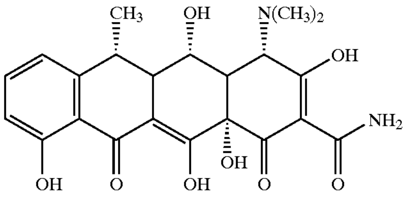 | * |

TABLE 1-continued

| Compound | Inhibition |
| --- | --- |
| 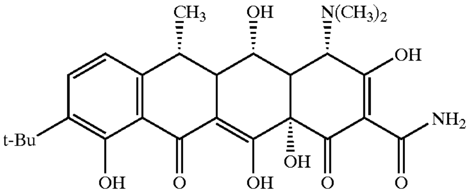 | ** |
| 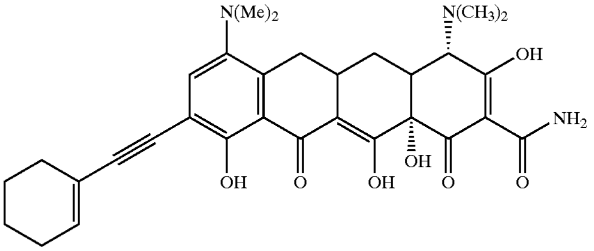 | ** |

Example 3

In Vitro Cytotoxicity Assay of Tetracycline Compounds

The following assay is designed to test the cytotoxicity of the tetracycline compounds of the invention on MDBK cells. Advantageous compounds of the invention are compounds with low cytotoxicity.

Cytotoxicity of the tetracycline compound is measured by the Cell Titer 96™ Aqueous, a non-radioactive cell proliferation assay, available as a commercial kit. It is a calorimetric method for determining the number of viable cells in proliferation or chemosensitivity assays. The assay is performed by growing MDBK cells in 96-well microliter plates, as in Example 2. Once confluent, the media is aspirated and replaced with 200 $\mu$L of media containing the tetracycline compound concentrations which were tested in Example 2. After 48 hour incubation, 40 $\mu$L/well of freshly prepared MTS/PMS solution is added. The plate is incubated for two hours at 37° C. and 8% $CO_2$ and then 100 $\mu$L of supernatant from each well is transferred to a new 96-well plate. The optical density is determined at 490 nm by an ELISA plate reader and the results are recorded and analyzed. Percent toxicity is calculated by subtracting the mean optical density (OD) of the medium control supernatants (no tetracycline compound) by the mean OD of the tetracycline compound supernatants and dividing by the OD of the medium control and multiplying by 100.

Example 4

In vivo Assay of Inhibition of *Cryptosporidium Parvum* Infection

This study is designed to test the ability of a tetracycline compound to control *Cryptosporidium parvum* infections in mice. Advantageous compounds of the invention control the *Cryptosporidium parvum* infection without killing the mice.

Three 4-week old C.B-17 SCID mice are randomized into six groups of seven mice each. Each animal receives a single I.P. injection of 1 mg of XMG1.2 mAb. Two hours later, mice in five of the six groups are infected with $10^7$ GCH1 oocysts via oral inoculation. Treatment with a tetracycline compounds begins on day 6, post infection, in two divided doses/day and continues for 10 days.

At the end of the experiment, all animals are necropsied and sections are taken from the pyloric region of the stomach, mid small intestine, terminal ileum, cecum, proximal colon, and liver/gal bladder for histological analysis to determine the extent of mucosal infection. Each site is assigned a score depending upon the extent of the infection. In this system, scores range from 0 (no infection) to 5 (extensive infection). Data is presented as the mean total score of the five sites. Oocyst shedding is monitored in all infected animals three times per week, beginning on day 4 of infection. Body weights are determined once per week throughout the course of study.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method for controlling *Cryptosporidium parvum* in a mammal, comprising administering to said mammal an effective amount of a tetracycline compound, such that *Cryptosporidium parvum* is controlled in said mammal, wherein said tetracycline compound is formula I:

(I)

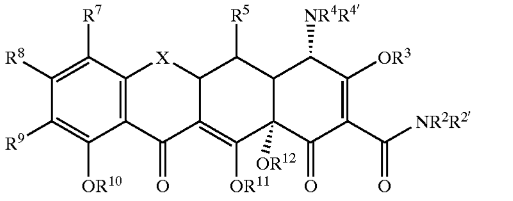

wherein:

X is $CHR^6$;

$R^2$, $R^4$ and $R^{4'}$ are each hydrogen, alkyl, alkenyl, alkoxy, alkylthio, alkylsulfinyl, alkylsulfonyl, arylalkyl, heterocyclic, or heteroaromatic;

$R^{2'}$, $R^3$, $R^{10}$, $R^{11}$, and $R^{12}$, are each hydrogen;

$R^5$ is hydroxy, hydrogen, thio, alkanoyl, aroyl, alkyl, heteroaromatic, alkyl, alkenyl, alkynyl, alkoxy, alkylthio, alkylsulfinyl, alkylsulfonyl, alkylamino, or an arylalkyl;

$R^6$, $R^7$, and $R^8$, are each independently hydrogen, hydroxyl, halogen, thio, alkyl, alkenyl, alkynyl, aryl, alkoxy, alkylthio, alkylsulfinyl, alkylsulfonyl, alkylamino, or an arylalkyl;

$R^9$ is alkyl or alkenyl, and pharmaceutically acceptable salts thereof.

2. The method of claim 1, wherein $R^2$, $R^{2'}$, $R^3$, $R^{10}$, $R^{11}$, and $R^{12}$, are each hydrogen.

3. The method of claim 1, wherein $R^4$ and $R^{4'}$ are each alkyl.

4. The method of claim 1, wherein $R^4$ and $R^{4'}$ are each methyl.

5. The method of claim 1, wherein $R^5$ is hydroxyl.

6. The method of claim 1, wherein $R^6$ is alkyl.

7. The method of claim 6, wherein $R^6$ is methyl.

8. The method of claim 1, wherein $R^9$ cyclopentenyl.

9. The method of claim 1, wherein said tetracycline compound is of the formula:

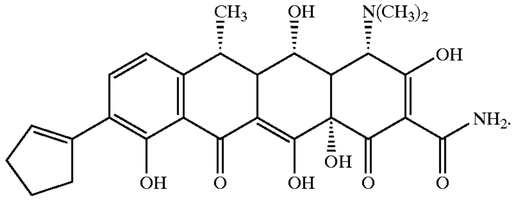

10. The method of claim 1, wherein said mammal is immunocompetent.

11. The method of claim 1, wherein said mammal is immunocompromised.

12. The method of claim 1, wherein said mammal is a human.

13. The method of claim 12, wherein said human has an immunodeficiency.

14. The method of claim 13, wherein said human has AIDS.

15. The method of claim 13, wherein said human has undergone chemotherapy.

16. The method of claim 1, wherein said effective amount is effective to treat a *Cryptosporidium parvum* related disorder in said mammal.

17. The method of claim 14, wherein said *Cryptosporidium parvum* related disorder is diarrhea.

18. The method of claim 14, wherein said *Cryptosporidium parvum* related disorder is cryptosporidiosis.

19. The method of claim 1, wherein said tetracycline compound inhibits more than 70% of *Cryptosporidium parvum* at a concentration less than 1 $\mu$g/ml.

20. A method for treating a *Cryptosporidium parvum* related disorder in a mammal, comprising administering to said mammal an effective amount of a tetracycline compound such that said mammal is treated for said disorder, wherein said tetracycline compound is of formula I:

(I)

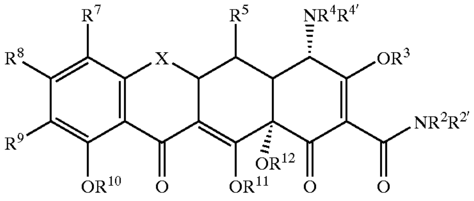

wherein:

X is $CHR^6$;

$R^2$, $R^4$ and $R^{4'}$ are each hydrogen, alkyl, alkenyl, alkoxy, alkylthio, alkylsulfinyl, alkylsulfonyl, arylalkyl, heterocyclic, or heteroaromatic;

$R^{2'}$, $R^3$, $R^{10}$, $R^{11}$, and $R^{12}$, are each hydrogen;

$R^5$ is hydroxy, hydrogen, thio, alkanoyl, aroyl, alkyl, heteroaromatic, alkyl, alkenyl, alkynyl, alkoxy, alkylthio, alkylsulfinyl, alkylsulfonyl, alkylamino, or an arylalkyl;

$R^6$, $R^7$, and $R^8$, are each independently hydrogen, hydroxyl, halogen, thio, alkyl, alkenyl, alkynyl, aryl, alkoxy, alkylthio, alkylsulfinyl, alkylsulfonyl, alkylamino, or an arylalkyl;

$R^9$ is alkyl or alkenyl, and pharmaceutically acceptable salts thereof.

21. The method of claim 20, wherein $R^2$, $R^{2'}$, $R^3$, $R^{10}$, $R^{11}$, and $R^{12}$, are each hydrogen.

22. The method of claim 21, wherein $R^4$ and $R^{4'}$ are each methyl.

23. The method of claim 22, wherein $R^5$ is alkanoyl, an ester group, a hydroxyl group or hydrogen.

24. The method of claim 20, wherein $R^6$ is alkyl.

25. The method of claim 20, wherein $R^9$ is cyclopentenyl.

26. The method of claim 20, wherein said tetracycline compound is 9-cyclopent-1-enyl-doxycycline.

27. The method of claim 20, wherein said mammal is immunocompetent.

28. The method of claim 20, wherein said mammal is immunocompromised.

29. The method of claim 20, wherein said mammal is a human.

30. The method of claim 29, wherein said human is immunodeficient.

31. The method of claim 30, wherein said human has AIDS.

32. The method of claim 30, wherein said human has undergone chemotherapy.

33. The method of claim 20, wherein said effective amount is effective to treat a *Cryptosporidium parvum* related disorder in said mammal.

34. The method of claim 33, wherein said *Cryptosporidium parvum* related disorder is diarrhea.

35. The method of claim 33, wherein said *Cryptosporidium parvum* related disorder is cryptosporidiosis.

36. The method of claim 20, further comprising the administration of a pharmaceutically acceptable carrier.

37. The method of claim 20, further comprising the administration of a supplementary anti-*Cryptosporidium parvum* agent.

38. The method of claim 20, wherein said supplementary agent is paromomycin.

* * * * *